(12) United States Patent
Chon et al.

(10) Patent No.: US 11,865,245 B2
(45) Date of Patent: Jan. 9, 2024

(54) IRRIGATION SLEEVE FOR OPHTHALMIC PROCEDURES

(71) Applicant: Alcon Inc., Fribourg (CH)

(72) Inventors: James Y. Chon, Irvine, CA (US); Andrea Kim, Irvine, CA (US)

(73) Assignee: Alcon Inc., Fribourg (CH)

( * ) Notice: Subject to any disclaimer, the term of this patent is extended or adjusted under 35 U.S.C. 154(b) by 396 days.

(21) Appl. No.: 17/083,642

(22) Filed: Oct. 29, 2020

(65) Prior Publication Data
US 2021/0128800 A1    May 6, 2021

Related U.S. Application Data

(60) Provisional application No. 62/930,252, filed on Nov. 4, 2019.

(51) Int. Cl.
*A61M 1/00* (2006.01)
*A61F 9/007* (2006.01)

(52) U.S. Cl.
CPC ......... *A61M 1/774* (2021.05); *A61F 9/00745* (2013.01); *A61M 2205/0216* (2013.01); *A61M 2210/0612* (2013.01)

(58) Field of Classification Search
CPC ............. A61F 9/00745; A61F 9/00763; A61B 2017/320084; A61B 2017/32007
See application file for complete search history.

(56) References Cited

U.S. PATENT DOCUMENTS 3,589,363 A    6/1971 Banko et al.
3,945,375 A *  3/1976 Banko ................. A61F 9/00763
                                                        606/49

(Continued)

FOREIGN PATENT DOCUMENTS

WO    WO-2009030974 A1 *  3/2009  ........ A61M 5/31513

OTHER PUBLICATIONS

R.L Clough, High-energy radiation and polymers: A review of commercial processes and emerging applications, Nuclear Instruments and Methods in Physics Research Section B: Beam Interactions with Materials and Atoms, vol. 185, Issues 1-4, 2001, pp. 8-33 (Year: 2001).*

(Continued)

*Primary Examiner* — Scott J Medway
(74) *Attorney, Agent, or Firm* — Patterson + Sheridan, LLP (57) ABSTRACT

Devices and methods are disclosed for improved irrigation sleeves for ophthalmic instruments to prevent or reduce the likelihood of the irrigation sleeve twisting and/or buckling upon inserting the irrigation sleeve into the eye. In some embodiments, an irrigation sleeve comprises a side opening for irrigation having an elongated shape, wherein the elongated shape is longer in a direction parallel to the longitudinal axis of the distal tube of the irrigation sleeve than in a direction around a circumference of the distal tube of the irrigation sleeve. In some embodiments, an irrigation sleeve comprises at least one rib on an internal surface of the distal end of the irrigation sleeve. In some embodiments, the irrigation sleeve has been subjected to one or more manufacturing steps adapted to stiffen the irrigation sleeve, such as being coated with a stiffening coating or being treated by being exposed to gamma irradiation.

15 Claims, 3 Drawing Sheets

(56) References Cited

U.S. PATENT DOCUMENTS

| | | | |
|---|---|---|---|
| 4,223,676 A | | 9/1980 | Wuchinich et al. |
| 4,246,902 A | | 1/1981 | Martinez |
| 4,493,694 A | | 1/1985 | Wuchinich |
| 4,515,583 A | | 5/1985 | Sorich |
| 4,589,415 A | | 5/1986 | Haaga |
| 4,609,368 A | | 9/1986 | Dotson, Jr. |
| 4,787,889 A | * | 11/1988 | Steppe ............... A61F 9/00745 604/35 |
| 4,808,154 A | * | 2/1989 | Freeman ............ A61F 9/00745 604/22 |
| 4,869,715 A | | 9/1989 | Sherburne |
| 4,922,902 A | | 5/1990 | Wuchinich et al. |
| 4,983,160 A | * | 1/1991 | Steppe ............... A61F 9/00745 604/35 |
| 5,094,876 A | * | 3/1992 | Goldberg ............ A61F 2/0077 522/167 |
| 5,178,605 A | | 1/1993 | Imonti |
| 5,188,589 A | * | 2/1993 | Wypych ............. A61F 9/00745 606/128 |
| 5,634,912 A | * | 6/1997 | Injev ..................... A61M 1/85 604/264 |
| 5,725,495 A | * | 3/1998 | Strukel ............... A61M 1/7413 604/35 |
| 5,807,310 A | * | 9/1998 | Hood .................. A61F 9/00745 606/107 |
| 5,941,887 A | * | 8/1999 | Steen ................. A61F 9/00745 606/107 |
| 6,013,046 A | * | 1/2000 | Maaskamp ......... A61F 9/00745 604/524 |
| 6,602,193 B2 | | 8/2003 | Chon |
| 7,572,242 B2 | | 8/2009 | Boukhny |
| 7,601,136 B2 | † | 10/2009 | Akahoshi |
| 7,651,490 B2 | | 1/2010 | Boukhny et al. |
| 8,267,891 B2 | * | 9/2012 | Dimalanta ......... A61F 9/00736 604/167.04 |
| 8,282,594 B2 | † | 10/2012 | Perkins |
| 8,814,894 B2 | | 8/2014 | Boukhny |
| 9,155,862 B2 | * | 10/2015 | Bellisario ........... A61M 25/007 |
| 9,789,282 B2 | * | 10/2017 | McKinnon ........ A61M 25/0009 |
| 10,213,533 B2 | † | 2/2019 | Walter |
| 10,232,092 B2 | * | 3/2019 | McClain ............... A61L 31/10 |
| 10,398,813 B2 | * | 9/2019 | Sforza ..................... A61M 1/89 |
| 10,406,275 B2 | * | 9/2019 | Wiljanen .............. A61M 3/022 |
| 2006/0052758 A1 | * | 3/2006 | Dewey ............... A61F 9/00745 604/272 |
| 2006/0135975 A1 | | 6/2006 | Perkins |
| 2007/0149950 A1 | * | 6/2007 | Perkins .............. A61F 9/00745 604/524 |
| 2008/0154218 A1 | † | 6/2008 | Gomez |
| 2008/0234709 A1 | * | 9/2008 | Houser ......... A61B 17/320068 606/169 |
| 2008/0249412 A1 | * | 10/2008 | Huang ................... A61B 8/483 600/442 |
| 2008/0300531 A1 | * | 12/2008 | Gills, Jr. ............. A61F 9/00736 604/22 |
| 2010/0160851 A1 | † | 6/2010 | Dimalanta |
| 2010/0324503 A1 | * | 12/2010 | McKinnon ........ A61M 25/0009 604/246 |
| 2011/0077624 A1 | * | 3/2011 | Brady ................. A61F 9/00736 606/4 |
| 2012/0157934 A1 | * | 6/2012 | Liao .................... A61F 9/00745 604/264 |
| 2012/0303118 A1 | * | 11/2012 | DeBoer .................. A61F 9/007 623/6.13 |
| 2015/0112356 A1 | | 4/2015 | Chon |
| 2015/0119915 A1 | * | 4/2015 | Neurohr ......... A61B 17/320068 606/169 |
| 2017/0172686 A1 | * | 6/2017 | Liou ..................... A61L 31/048 |
| 2019/0060534 A1 | | 2/2019 | Banko |
| 2019/0298571 A1 | * | 10/2019 | McDonell ........... A61F 9/00745 |

OTHER PUBLICATIONS

Palsule, A.S., Clarson, S.J. & Widenhouse, C.W. Gamma Irradiation of Silicones. J Inorg Organomet Polym 18, 207-221 (2008). https://doi.org/10.1007/s10904-008-9205-0 (Year: 2008).*

Satti, A. J., Ressia, J. A., Cerrada, M. L., Andreucetti, N. A., and Vallés, E. M., Rheological analysis of irradiated crosslinkable and scissionable polymers used for medical devices under different radiation conditions. Radiation Physics and Chemistry 144, 298-303, 2018 (Year: 2018).*

Abbott Medical Optics Inc., AMO Phacoemulsification Tip and Irrigation Sleeve 510(k) Premarket Notification Oct. 15, 2012. https://www.accessdata.fda.gov/cdrh_docs/pdf12/K121721.pdf.†

Saint-Gobain Performance Plastics, Effect of Sterilization on the Mechanical Properties of Silicone Rubbers, 2009. https://www.biopharm.saint-gobain.com/sites/imdf.biopharm.com/files/effect-of-sterilization-on-the-mechanical-properties-of-silicone-rubbers.pdf (Available on archive.org on Oct. 29, 2016 at https://web.archive.org/web/20161029200513/https://bioprocessintl.com/manufacturing/monoclonal-antibodies/effect-of-sterilization-on-the-mechanical-properties-of-silicone-rubbers-239379/).†

Palsule, A.S., Clarson, S.J., & Widenhouse, C.W. Gamma Irradiation of Silicones, Journal of Inorganic Polymers and Materials 18, 207-221 (2008).†

Bausch & Lomb Inc., Bausch & Lomb Irrigation and Aspiration Handpieces 510(k) Summary Statement, Mar. 12, 2008 https://www.accessdata.fda.gov/cdrh_docs/pdf7/k073023.pdf.†

Egert, D., Peterson, R.L., Najafi, K. Parylene microprobes with engineered stiffness and shape for improved insertion. Proceedings of the 16th International Conference on Solid-State Sensors, Actuators and Microsystems—Transducers, Beijing, China, Jun. 5-9, 2011, 198-201.†

* cited by examiner
† cited by third party

IRRIGATION SLEEVE FOR OPHTHALMIC PROCEDURES

TECHNICAL FIELD

The present disclosure is directed to irrigation sleeves used in ophthalmic procedures.

BACKGROUND

A number of different ophthalmic procedures are performed in which an instrument with an irrigation sleeve is inserted into the eye for performing all or part of the procedure. For example, ophthalmic phacoemulsification is a procedure commonly used for removal of cataractous lenses. The procedure typically involves insertion of the working tip of an ultrasonic handpiece into the eye. In such handpieces, ultrasonic vibrations drive the working tip which the physician can maneuver against the cataractous lens in order to break up or emulsify the lens for removal and replacement.

Ultrasonic ophthalmic phacoemulsification handpieces in common use typically are designed not only to drive the ultrasonic working tip but also to perform additional functions, such as to facilitate supplying irrigation fluid into the eye and to facilitate aspiration of fluid and of the fragmented or emulsified lens from the eye. To facilitate the irrigation function, such ultrasonic handpieces may include an irrigation sleeve around the working tip for directing the irrigation fluid. The handpiece may be connected to a control console by one or more electric cables and flexible tubes. The electric cable supplies power to the components for driving vibration of the working tip, while the tubes serve as conduits for the irrigation fluid supplied to the eye and for the aspirated fluid drawn from the eye.

A number of different ultrasonic handpieces and working tips have been proposed and used. Some examples of ultrasonic handpieces and working tips are described and shown, for example, in U.S. Pat. Nos. 3,589,363; 4,223,676; 4,246,902; 4,493,694; 4,515,583; 4,589,415; 4,609,368; 4,869,715; 4,922,902; 5,178,605; 6,602,193; 7,572,242; 7,651,490; and 8,814,894; the entire contents of these U.S. Patents are incorporated herein by reference.

In addition to ultrasonic phacoemulsification, other ophthalmic procedures may be performed in which an instrument with an irrigation sleeve is inserted into the eye for performing all or part of the procedure. The irrigation sleeve may be placed around the working tip of the instrument so that the distal end of the working tip of the instrument extends through a distal opening in the end of the irrigation sleeve. Irrigation occurs by delivering irrigation fluid through the sleeve, which exits through a relatively large circular side opening proximate the distal end of the irrigation sleeve.

Prior irrigation sleeves on occasion can experience twisting and/or buckling upon inserting the sleeve into the eye through an incision in the eye. This twisting and/or buckling is disadvantageous, as it can cause issues such as difficulty in inserting the instrument into the eye, potential irritation or damage to the eye at the insertion site, mispositioning of the irrigation sleeve, potential interference with functioning of the instrument, and/or potential interference with or blocking of the irrigation flow path.

There is a continued need for improved irrigation sleeves for ophthalmic procedures and associated methods of use.

SUMMARY

The present disclosure is directed to improved designs for irrigation sleeves for ophthalmic procedures and associated methods.

In some embodiments, an irrigation sleeve for an ophthalmic instrument comprises a proximal hub adapted to be coupled to a housing of the ophthalmic instrument and a distal tube adapted to fit around a working tip of the ophthalmic instrument, the distal tube having a longitudinal axis, a distal end, an end opening at its distal end adapted to fit around a distal end of the working tip projecting therethrough, and a side opening at its distal end proximate to the end opening adapted for irrigation fluid to flow therethrough; wherein the side opening has an elongated shape, wherein the elongated shape is longer in a direction parallel to the longitudinal axis of the distal tube of the irrigation sleeve than in a direction around a circumference of the distal tube of the irrigation sleeve. The irrigation sleeve may be comprised of an elastomeric material, such as silicone rubber.

In some embodiments, the side opening is shaped as an elongated slot. The elongated slot may have a length in the direction parallel to the longitudinal axis of the distal tube of the irrigation sleeve and a width in the direction around the circumference of the distal tube of the irrigation sleeve, wherein the length of the elongated slot is greater than the width of the elongated slot. The elongated slot may comprise a curved leading edge, two relatively straight sides, and a curved trailing edge.

In some embodiments, the side opening is shaped as a teardrop. The teardrop may have a length in the direction parallel to the longitudinal axis of the distal tube of the irrigation sleeve and a width in the direction around the circumference of the distal tube of the irrigation sleeve, wherein the length of the teardrop is greater than the width of the teardrop. The teardrop may comprise a point at its leading edge, two relatively straight sides from the leading edge to an area of largest width of the teardrop, and a curved trailing edge.

In some embodiments, the side opening is shaped as an oval. The oval may have a length in the direction parallel to the longitudinal axis of the distal tube of the irrigation sleeve and a width in the direction around the circumference of the distal tube of the irrigation sleeve, wherein the length of the oval is greater than the width of the oval.

In some embodiments, an irrigation sleeve for an ophthalmic instrument comprises a proximal hub adapted to be coupled to a housing of the ophthalmic instrument and a distal tube adapted to fit around a working tip of the ophthalmic instrument, the distal tube having a longitudinal axis, a distal end, an end opening at its distal end adapted to fit around a distal end of the working tip projecting therethrough, and a side opening at its distal end proximate to the end opening adapted for irrigation fluid to flow therethrough; wherein the irrigation sleeve further comprises at least one rib on an internal surface of the distal end of the distal tube of the irrigation sleeve. The rib or ribs may be located adjacent the side opening, at the same location along the longitudinal length of the irrigation sleeve as the side opening. The rib or ribs may be elongated in a direction parallel to the longitudinal axis of the distal tube of the irrigation sleeve. A plurality of ribs may be distributed circumferentially around the internal surface of the distal end of the distal tube of the irrigation sleeve.

In some embodiments, an irrigation sleeve for an ophthalmic instrument comprises a proximal hub adapted to be coupled to a housing of the ophthalmic instrument and a distal tube adapted to fit around a working tip of the ophthalmic instrument, the distal tube having a longitudinal axis, a distal end, an end opening at its distal end adapted to fit around a distal end of the working tip projecting therethrough, and a side opening at its distal end proximate to the end opening adapted for irrigation fluid to flow therethrough; wherein the irrigation sleeve comprises an elastomeric material and wherein the irrigation sleeve has been subjected to one or more manufacturing steps adapted to stiffen the irrigation sleeve. In some embodiments, the irrigation sleeve has been coated with a stiffening coating, such as a parylene coating. In some embodiments, the irrigation sleeve has been treated by being exposed to gamma irradiation.

Embodiments are disclosed herein for improved irrigation sleeves for ophthalmic instruments to prevent or reduce the likelihood of the irrigation sleeve twisting and/or buckling upon inserting the irrigation sleeve into the eye.

BRIEF DESCRIPTION OF THE DRAWINGS

The accompanying drawings illustrate implementations of the devices and methods disclosed herein and, together with the description, serve to explain the principles of the present disclosure.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

Figure 1:
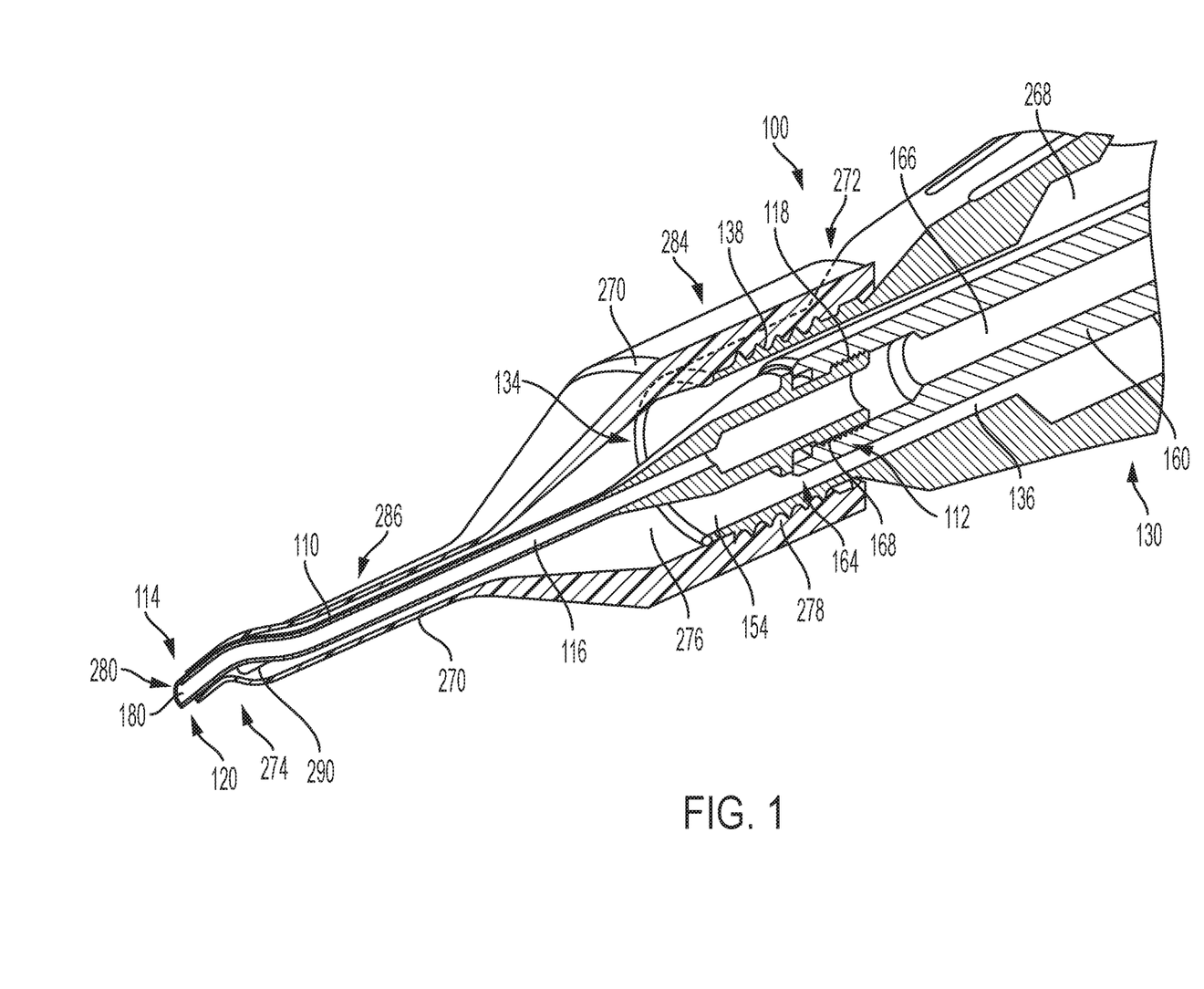
FIG. 1 shows a perspective view in cross-section of the distal end of an ophthalmic instrument with an irrigation sleeve in place.

FIG. 1 shows a perspective view in cross-section of the distal end of an ophthalmic instrument 100 with an irrigation sleeve 270 in place as part of the ophthalmic instrument 100. In this example, the ophthalmic instrument is an ultrasonic handpiece as may be used in a phacoemulsification procedure, although ophthalmic instruments for other ophthalmic procedures may be used with an irrigation sleeve as described herein. An example of a suitable ultrasonic handpiece is the OZIL® Torsional Handpiece of Alcon, headquartered in Fort Worth, Tex.

The ophthalmic instrument 100 comprises a housing 130 having a proximal end (to the right in FIG. 1) and a distal end 134, a working tip 110 that extends from the distal end 134 of the housing 130, and an ultrasonic horn 160 positioned within the housing 130. A proximal end 112 of the working tip 110 is connected to the distal end 164 of the ultrasonic horn 160. The connection between the working tip 110 and the ultrasonic horn 160 may be made by any suitable connection. For example, the proximal end 112 of the working tip 110 may have threads 118 and the distal end 164 of the ultrasonic horn 160 may have threads 168 by which the working tip 110 may be connected to the ultrasonic horn 160. A distal end 114 of the working tip 110 comprises a working end 120 for performing a desired operation, such as a phacoemulsification procedure in an ophthalmic phacoemulsification handpiece. In the illustrated example, the working end 120 is bent or angled.

The housing 130 is hollow and defines an internal hollow chamber 136 in which internal components of the ophthalmic instrument 100 are housed and protected. The housing 130 has an external surface that can be grasped by an operator of the ultrasonic handpiece 100, such as a surgeon. At its distal end 134, the housing 130 has an opening 154 through which the working tip 110 extends.

The ultrasonic horn 160 and working tip 110 are generally aligned along a longitudinal axis of the ophthalmic instrument 100. The longitudinal axis extends in a longitudinal direction, and each of the ultrasonic horn 160 and the working tip 110 has a longitudinal axis that is aligned with the longitudinal axis of the ophthalmic instrument 100.

The ultrasonic horn 160 has a channel 166 extending longitudinally through the ultrasonic horn 160, and the working tip 110 has a channel 116 extending longitudinally through the working tip 110. The working tip 110 has an opening 180 at its distal end 114. The opening 180 at the distal end 114 of the working tip 110 and the channels 116, 166 provide an aspiration passageway for aspiration of fluid and/or particles away from the eye. For example, by applying suction through the aspiration passageway, fluid and/or tissue, such as lens or other tissue fragments in a phacoemulsification procedure, may be aspirated through the opening 180 in the distal end 114 of the working tip 110 and through the channels 116 and 166.

The irrigation sleeve 270 serves to direct an irrigation fluid, e.g., saline, to the distal end 114 of the working tip 110. The housing 130 has an irrigation supply line 268 through which an irrigation fluid may be introduced. The irrigation sleeve 270 may be coupled directly to the housing 130 or coupled to the housing 130 through another part of the ophthalmic instrument 100. In the illustrated example, the housing 130 has external threads 138 at its distal end 134, and the irrigation sleeve 270 has internal threads 278 at its proximal end 272 by which the irrigation sleeve 270 may be attached to the housing 130. The irrigation sleeve 270 is positioned around the working tip 110 to provide a fluid passageway or channel 276 from the position of its attachment to the housing 130 through the space between the irrigation sleeve 270 and the working tip 110. As can be seen in FIG. 1, the irrigation sleeve generally has a proximal hub 284 having a relatively larger diameter for coupling to the housing 130 and a distal tube 286 in the shape of a narrow tube having a relatively smaller diameter for fitting around the working tip 110 at a small enough dimension for inserting through an incision in an eye.

The irrigation sleeve 270 has an end opening 280 at its distal end 274 through which the distal end 114 of the working tip 100 projects. At the end opening 280, the irrigation sleeve has a snug fit around the working tip 100. The irrigation sleeve also has a side opening 290 at its distal end 274, proximate to the end opening 280 and the distal end 114 of the working tip 110. When an irrigation fluid is introduced through the supply line 268 in the housing 130, it passes through the channel 276 of the irrigation sleeve 270 and out of the side opening 290 at the distal end 274 of the irrigation sleeve 270.

For operation, the ophthalmic instrument 100 may be connected to a control console. For example, the ophthalmic instrument 100 may be connected to a control console like the control console of the CENTURION® Vision System of Alcon, headquartered in Fort Worth, Tex., or any other suitable control console. The ophthalmic instrument 100 may be connected to the control console by one or more electric cables, for example one or more electric cables that are used for supplying current to a set of piezoelectric crystals for driving the ultrasonic horn 160. The ophthalmic instrument 100 may also be connected to the control console by one or more tubes, for example one or more tubes that may supply an irrigation fluid from the control console to the proximal end of the irrigation supply line 268 of the housing 130.

In operation of the device, the operator inserts the working tip 110 with the irrigation sleeve 270 around it through an incision in the eye. The operator positions the working end 120 of the working tip 110 at a desired location, such as adjacent a cataractous lens of a patient. Irrigation fluid such as saline may be supplied from the control console through the irrigation supply line 268 and irrigation sleeve 270. The set of piezoelectric crystals may be activated by supplying electrical current from the control console to electrical wiring that connects to the set of piezoelectric crystals, and the activation of the piezoelectric crystals induces vibration of the ultrasonic horn 160. The vibration of the ultrasonic horn 160 causes vibration of the attached working tip 110, which can break up or phacoemulsify the desired tissue such as the cataractous lens. At the same time, a pumping module may be used to apply suction through the aspiration channel including channel 166 of the ultrasonic horn 160 and channel 116 of the working tip 110, thereby suctioning away fluid and tissue and/or lens fragments through the opening 180 at the distal end 114 of the working tip 110.

The distal tube 286 of the irrigation sleeve 270 may have an outer diameter in a range of 0.030 inches to 0.080 inches to fit through an incision in an eye and an inner diameter in a range of 0.020 inches to 0.070 inches to accommodate the working tip 110 within it. The end opening 280 at the distal end 274 of the irrigation sleeve 270 through which the distal end 114 of the working tip 100 projects may be a circular opening having a diameter in a range of 0.010 inches to 0.065 inches, which may be equal to or slightly smaller than the outer diameter of the distal end 114 of the working tip 100 to form a snug fit around the distal end 114 of the working tip 100. The examples of dimensions and ranges of dimensions represent possible embodiments; other embodiments with different dimensions may be used.

The irrigation sleeve 270 may be made of an elastomeric material such as a compliant silicone rubber. The irrigation sleeve 270 alternatively may be made of other materials, such as polyurethane, ethylene propylene, neoprene, or other suitable materials. An elastomeric material for the irrigation sleeve 270 allows some compliance and facilitates the snug fit between irrigation sleeve 270 and the working tip 110 at the area of the end opening 280. An elastomeric material for the irrigation sleeve 270 also facilitates a seal or snug fit between the irrigation sleeve 270 and the adjacent eye tissue at the incision site, such as the cornea or sclera, which can help minimize leakage from the eye between the eye tissue and the irrigation sleeve 270.

Figure 2:
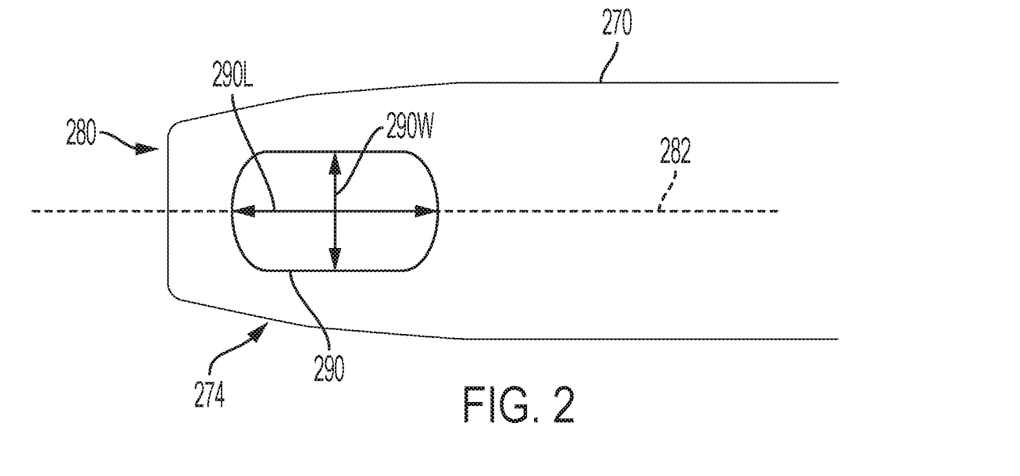
FIG. 2 shows a side view of the distal end of the irrigation sleeve of FIG. 1.

The irrigation sleeve 270 may have one or more features designed to prevent and/or reduce the likelihood of the irrigation sleeve 270 twisting and/or buckling upon inserting the irrigation sleeve 270 into the eye through the incision in the eye. In the example shown in FIGS. 1 and 2, the side opening 290 through which irrigation fluid exits at the distal end 274 of the irrigation sleeve 270 is shaped as an elongated slot. The elongated slot is elongated in the direction of the longitudinal axis 282 of the irrigation sleeve 270, which extends parallel to the channel 276 of the irrigation sleeve 270 and, when the irrigation sleeve 270 is attached to the remainder of the ophthalmic instrument 100, parallel to the longitudinal axis of the ophthalmic instrument 100. The length 290L of the elongated slot is the dimension of the elongated slot taken in the direction parallel to the longitudinal axis 282 of the irrigation sleeve 270, and the length 290L of the elongated slot is greater than the width 290W of the elongated slot, which is the dimension of the elongated slot taken in the direction around the circumference of the irrigation sleeve 270. As an example, the length 290L of the elongated slot may be in a range of 0.020 inches to 0.150 inches, and the width 290W of the elongated slot may be in a range of 0.010 inches to 0.065 inches. As stated above, the examples of dimensions and ranges of dimensions represent possible embodiments; other embodiments with different dimensions may be used. The elongated slot as illustrated in FIG. 2 has two relatively straight sides, a curved leading edge, and a curved trailing edge (leading and trailing taken in the direction of insertion of the irrigation sleeve 270 into an eye), although other shapes for the elongated slot are possible.

The shape and dimensions of the side opening 290 in the form of an elongated slot as shown and described help to prevent or reduce the likelihood of the irrigation sleeve 270 twisting and/or buckling upon inserting the irrigation sleeve 270 into the eye through the incision in the eye. The elongation of the slot in the direction of the length 290L, which is the direction of insertion of the irrigation sleeve through the eye incision, allows for the area of the side opening 290 to remain sufficiently large for efficient irrigation while at the same time allowing for the width 290W of the elongated slot to be kept relatively small. Keeping the width 290W relatively small helps keep the irrigation sleeve 270 sufficiently stiff in the area of the side opening 290 to prevent or reduce the likelihood of the irrigation sleeve 270 twisting and/or buckling upon inserting the irrigation sleeve 270 into the eye. Because of the relatively small width 290W, any given cross-section of the irrigation sleeve 270 taken perpendicular to the longitudinal axis 282 through the side opening 290 will have a larger amount of material (as compared to a larger width of the side opening 290), which in turn serves to keep the irrigation sleeve 270 relatively stiff.

Figure 3:
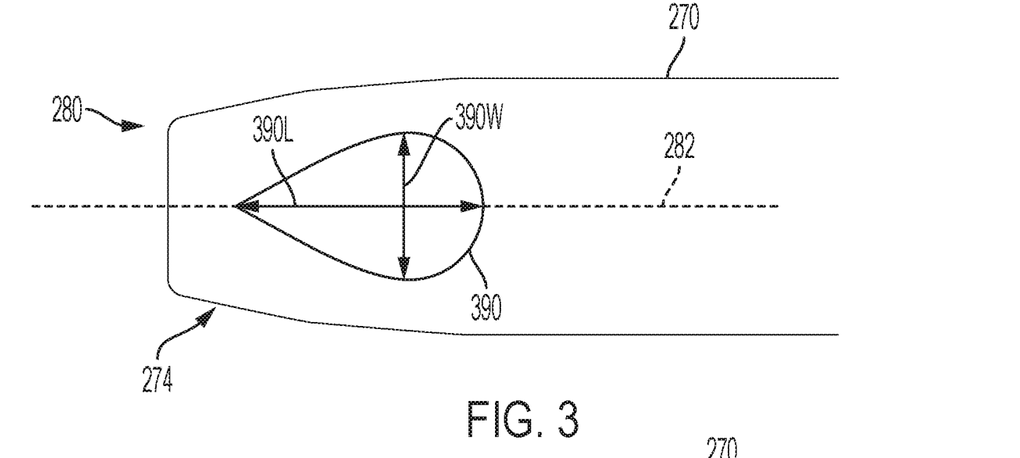
FIG. 3 shows a side view of the distal end of another embodiment of an irrigation sleeve.

FIG. 3 shows an alternative embodiment for the irrigation sleeve 270 in which all features may be the same as shown and described above with respect to FIGS. 1 and 2 except that the shape and size of the side opening is different. In the example shown in FIG. 3, the side opening 390 through which irrigation fluid exits at the distal end 274 of the irrigation sleeve 270 is shaped as a teardrop. Like the elongated slot, the teardrop is elongated in the direction of the longitudinal axis 282 of the irrigation sleeve 270. The length 390L of the teardrop is the dimension of the teardrop taken in the direction parallel to the longitudinal axis 282 of the irrigation sleeve 270, and the length 390L of the teardrop is greater than the width 390W of the teardrop, which is the dimension of the teardrop taken in the direction around the circumference of the irrigation sleeve 270. As an example, the length 390L of the teardrop may be in a range of 0.020 inches to 0.150 inches, and the width 390W of the teardrop may be in a range of 0.010 inches to 0.065 inches. As stated above, the examples of dimensions and ranges of dimensions represent possible embodiments; other embodiments with different dimensions may be used. The teardrop shape as illustrated in FIG. 3 has a point at its leading edge with two sides relatively straight from the leading edge to the area of the largest width of the teardrop and a curved (e.g., semicircular) trailing edge, although other shapes for the teardrop are possible.

Like the elongated slot, the shape and dimensions of the side opening 390 in the form of a teardrop as shown and described helps to prevent or reduce the likelihood of the irrigation sleeve 270 twisting and/or buckling upon inserting the irrigation sleeve 270 into the eye through the incision in the eye. The teardrop is elongated in the direction of the length 390L, which is the direction of insertion of the irrigation sleeve through the eye incision, which allows for the area of the side opening 390 to remain sufficiently large for efficient irrigation while at the same time allowing for the width 390W of the teardrop to be kept relatively small. Keeping the width 390W relatively small helps keep the irrigation sleeve 270 sufficiently stiff in the area of the side opening 390 to prevent or reduce the likelihood of the irrigation sleeve 270 twisting and/or buckling upon inserting the irrigation sleeve 270 into the eye. Because of the relatively small width 390W, any given cross-section of the irrigation sleeve 270 taken perpendicular to the longitudinal axis 282 through the side opening 390 will have a larger amount of material (as compared to a larger width of the side opening 390), which in turn serves to keep the irrigation sleeve 270 relatively stiff.

Figure 4:
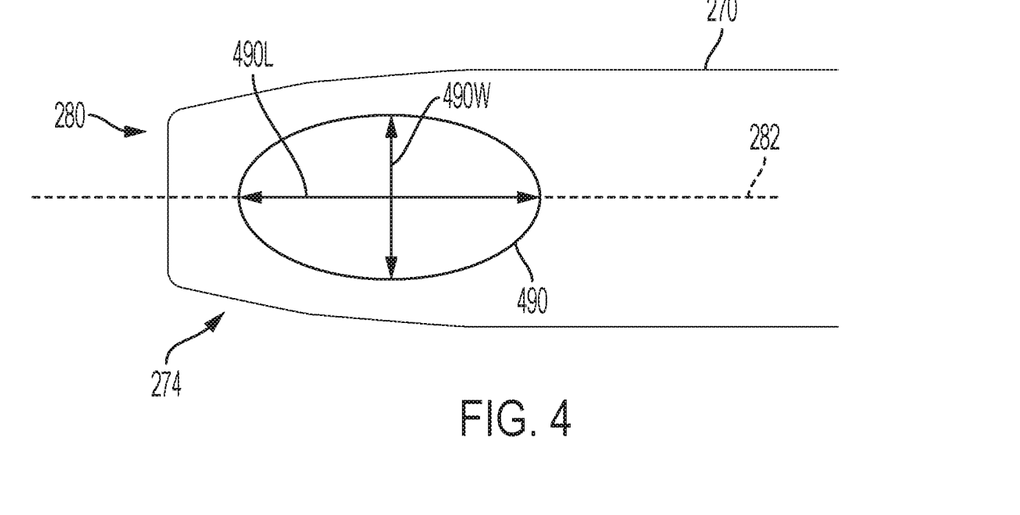
FIG. 4 shows a side view of the distal end of another embodiment of an irrigation sleeve.

FIG. 4 shows an alternative embodiment for the irrigation sleeve 270 in which all features may be the same as shown and described above with respect to FIGS. 1 and 2 except that the shape and size of the side opening is again different. In the example shown in FIG. 4, the side opening 490 through which irrigation fluid exits at the distal end 274 of the irrigation sleeve 270 is shaped as an oval. Like the elongated slot, the oval is elongated in the direction of the longitudinal axis 282 of the irrigation sleeve 270. The length 490L of the oval is the dimension of the oval taken in the direction parallel to the longitudinal axis 282 of the irrigation sleeve 270, and the length 490L of the oval is greater than the width 490W of the oval, which is the dimension of the oval taken in the direction around the circumference of the irrigation sleeve 270. As an example, the length 490L of the oval may be in a range of 0.020 inches to 0.150 inches, and the width 490W of the oval may be in a range of 0.010 inches to 0.065 inches. As stated above, the examples of dimensions and ranges of dimensions represent possible embodiments; other embodiments with different dimensions may be used.

Like the elongated slot, the shape and dimensions of the side opening 490 in the form of an oval as shown and described helps to prevent or reduce the likelihood of the irrigation sleeve 270 twisting and/or buckling upon inserting the irrigation sleeve 270 into the eye through the incision in the eye. The oval is elongated in the direction of the length 490L, which is the direction of insertion of the irrigation sleeve through the eye incision, which allows for the area of the side opening 490 to remain sufficiently large for efficient irrigation while at the same time allowing for the width 490W of the oval to be kept relatively small. Keeping the width 490W relatively small helps keep the irrigation sleeve 270 sufficiently stiff in the area of the side opening 490 to prevent or reduce the likelihood of the irrigation sleeve 270 twisting and/or buckling upon inserting the irrigation sleeve 270 into the eye. Because of the relatively small width 490W, any given cross-section of the irrigation sleeve 270 taken perpendicular to the longitudinal axis 282 through the side opening 490 will have a larger amount of material (as compared to a larger width of the side opening 490), which in turn serves to keep the irrigation sleeve 270 relatively stiff.

Other shapes for a side opening are possible within the scope of the disclosure in which the area of the side opening remains sufficiently large for efficient irrigation while at the same time allowing for the width of the side opening in the direction around the circumference of the irrigation sleeve to be kept relatively small. Some examples include rectangular, triangular, and elliptical, to name a few examples.

Figure 5:
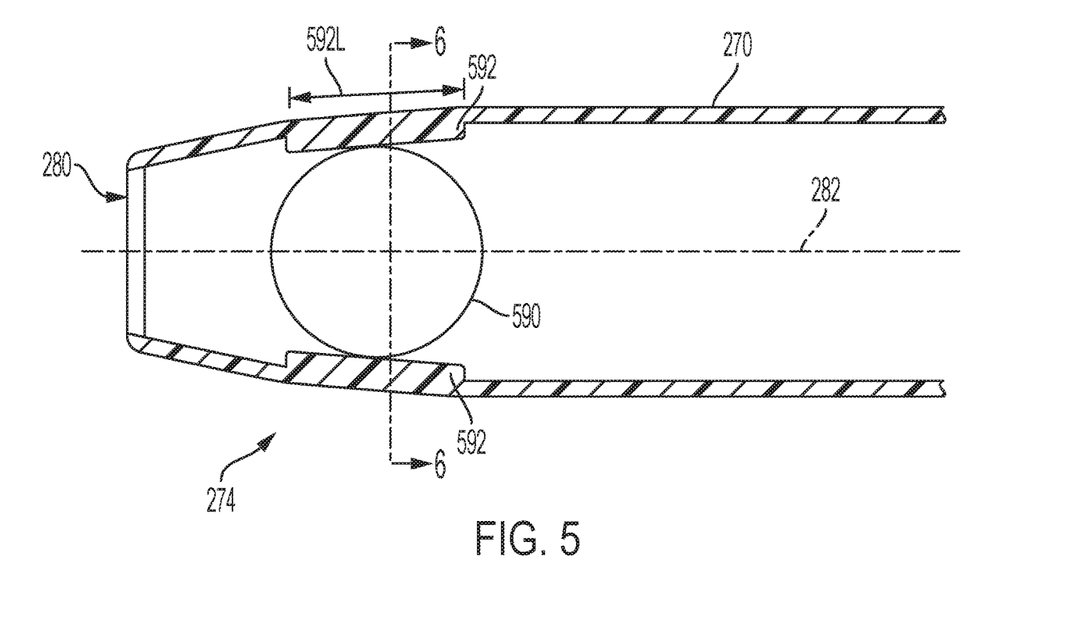
FIG. 5 shows a cross-sectional side view of the distal end of another embodiment of an irrigation sleeve.
Figure 6:
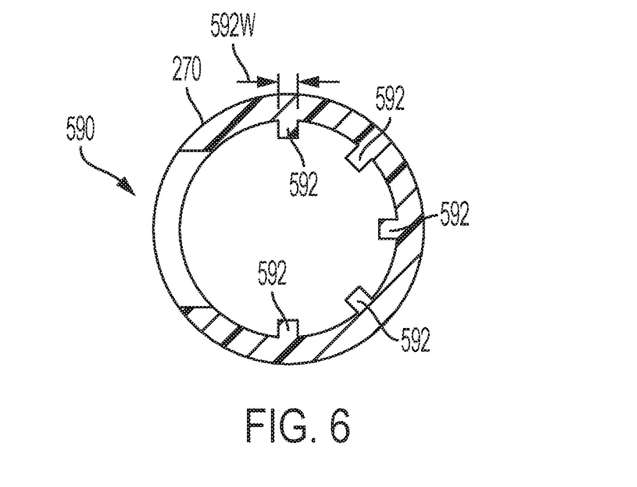
FIG. 6 shows a cross-sectional view of the irrigation sleeve of FIG. 5 taken along the line 6-6 in FIG. 5.

FIGS. 5 and 6 shows an alternative embodiment for an irrigation sleeve 270 in which all features may be the same as shown and described above with respect to FIGS. 1 and 2 except that the shape and size of the side opening may be different and stiffening ribs are included. In the example shown in FIGS. 5 and 6, the side opening 590 through which irrigation fluid exits at the distal end 274 of the irrigation sleeve 270 is shaped as a circle, although any of the alternative shapes illustrated and/or described herein may be used. The irrigation sleeve 270 in FIGS. 5 and 6 includes one or more stiffening ribs 592 on the internal surface of the distal end 274 of the irrigation sleeve 270. In the illustrated example, the ribs 592 are adjacent the side opening 590, located at or around the same location as the side opening 590 along the longitudinal length of the irrigation sleeve 270. The ribs 592 are spaced around the inner perimeter of the irrigation sleeve 270. The ribs 592 may be manufactured as integral parts of the irrigation sleeve 270, for example molded together with the remainder of the irrigation sleeve 270 out of the same material as the remainder of the irrigation sleeve 270. In the illustrated example, each of the ribs 592 is elongated in the direction of the longitudinal axis 282 of the irrigation sleeve 270. The ribs 592 may have any suitable shape, for example having a cross-section that is trapezoidal, square, rectangular, rounded, triangular, or any other suitable shape. The length 592L of a rib 592 is the dimension of the rib taken in the direction parallel to the longitudinal axis 282 of the irrigation sleeve 270, and the width 592W of a rib 592 is the dimension of the rib taken in the direction around the circumference of the irrigation sleeve 270. As an example, the length 592L of each rib 592 may be in a range of 0.020 inches to 0.150 inches, and the width 592W of each rib may be in a range of 0.001 inches to 0.010 inches. As stated above, the examples of dimensions and ranges of dimensions represent possible embodiments; other embodiments with different dimensions may be used.

The ribs 592 as shown and described help to prevent or reduce the likelihood of the irrigation sleeve 270 twisting and/or buckling upon inserting the irrigation sleeve 270 into the eye through the incision in the eye. The ribs 592 stiffen the irrigation sleeve 270 in the area of the side opening 590, thereby reinforcing the irrigation sleeve 270 in the area where it would otherwise be weak due to the absence of material at the location of the side opening. The ribs 592 may also be in contact with the working tip 110, which can also help to prevent or reduce the likelihood of the irrigation sleeve 270 twisting and/or buckling.

An irrigation sleeve as described herein may additionally or alternatively be stiffened in one or more other ways in order to prevent or reduce the likelihood of the irrigation sleeve twisting and/or buckling upon inserting the irrigation sleeve into the eye through the incision in the eye. For example, the irrigation sleeve may be subjected to one or more manufacturing steps adapted to stiffen the irrigation sleeve. As one example, the irrigation sleeve may be coated with a stiffening coating that makes the irrigation sleeve more resistant to twisting and/or buckling. One example of a suitable coating is a parylene coating, although other suitable coating materials may be used. The coating may be applied to the underlying irrigation sleeve material in any suitable thickness, for example about five microns.

As another example of a manufacturing step adapted to stiffen the irrigation sleeve, the irrigation sleeve may be treated by being exposed to gamma irradiation. For example, the irrigation sleeve may be exposed to one or more doses of 90 kGy or more in order to stiffen the sleeve. The irradiation increases the cross-linking of the polymer chain, which stiffens the irrigation sleeve.

These manufacturing steps, such as coating and/or exposure to radiation, are applied to an irrigation sleeve made of elastomeric or compliant material as described above. These steps serve to stiffen the irrigation sleeve while at the same time leaving the irrigation sleeve sufficiently resilient so that it forms an adequate seal around the distal end of the working tip and/or an adequate seal with the eye at the incision site, as described above.

As persons having ordinary skill in the art will appreciate, the devices and methods as disclosed herein have a number of advantages over the prior art. Such advantages include an irrigation sleeve that is resistant to twisting and/or buckling upon insertion of the irrigation sleeve into the eye. An irrigation sleeve as disclosed herein avoids disadvantages of the prior art, such as difficulty in inserting the instrument into the eye, irritation or damage to the eye at the insertion site, mispositioning of the irrigation sleeve, interference with functioning of the ophthalmic instrument, and/or potential interference with or blocking of the irrigation flow path. As a result, an irrigation sleeve as described herein may lead to more efficient procedures, improved chamber stability, lower cost, and/or improved patient outcome.

These advantages are particularly useful in allowing for procedures to use smaller incisions in the eye. Some ophthalmic procedures have utilized eye incisions of approximately 3.2 mm for example, and there have been efforts to use smaller incisions, such as 2.8 mm, 2.4 mm, or 2.2 mm, for example. A smaller incision can be less traumatic, can have fewer complications, and can lead to quicker healing. However, a smaller incision can require a smaller diameter and thinner irrigation sleeve, which can increase the likelihood of buckling and/or twisting of the irrigation sleeve. An irrigation sleeve as described herein allows for an irrigation sleeve that may be smaller and/or thinner to accommodate a smaller incision in the eye while at the same time being resistant to twisting and/or buckling. Thus, an irrigation sleeve as described herein can be used with smaller eye incisions, leading to the advantages of smaller eye incisions as described above.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An irrigation sleeve for an ophthalmic instrument, the irrigation sleeve comprising:
    a proximal hub adapted to be coupled to a housing of the ophthalmic instrument; and
    a distal tube adapted to fit around a working tip of the ophthalmic instrument, the distal tube having a longitudinal axis, a distal end, an end opening at the distal end of the distal tube adapted to fit around a distal end of the working tip projecting therethrough, and a side opening at the distal end of the distal tube proximate to the end opening adapted for irrigation fluid to flow therethrough;
        wherein the side opening has an elongated shape, wherein the elongated shape is longer in a direction parallel to the longitudinal axis of the distal tube of the irrigation sleeve than in a direction around a circumference of the distal tube of the irrigation sleeve; and
        wherein the side opening is shaped as a teardrop comprising a point at a leading distal edge of the teardrop, two substantially straight sides extending from the leading distal edge to an area of largest width of the teardrop, and a curved trailing edge disposed opposite the leading distal edge.

2. The irrigation sleeve of claim 1, wherein the teardrop has a length in the direction parallel to the longitudinal axis of the distal tube of the irrigation sleeve and a width in the direction around the circumference of the distal tube of the irrigation sleeve, and wherein the length of the teardrop is greater than the width of the teardrop.

3. The irrigation sleeve of claim 1, wherein the irrigation sleeve is comprised of an elastomeric material.

4. The irrigation sleeve of claim 3, wherein the irrigation sleeve is comprised of silicone rubber.

5. An irrigation sleeve for an ophthalmic instrument, the irrigation sleeve comprising:
    a proximal hub adapted to be coupled to a housing of the ophthalmic instrument; and
    a distal tube adapted to fit around a working tip of the ophthalmic instrument, the distal tube having a longitudinal axis, a distal end, an end opening at the distal end of the distal tube adapted to fit around a distal end of the working tip projecting therethrough, and a side opening at the distal end of the distal tube proximate to the end opening;
        wherein the irrigation sleeve further comprises at least one rib on an internal surface of the distal end of the distal tube of the irrigation sleeve, the at least one rib having a length parallel to a longitudinal length of the distal tube; and
        wherein the length of the at least one rib corresponds with a dimension of the side opening of the distal tube.

6. The irrigation sleeve of claim 5, wherein the at least one rib is located adjacent the side opening, at the same location along the longitudinal length of the irrigation sleeve as the side opening.

7. The irrigation sleeve of claim 5, wherein the at least one rib is elongated in a direction parallel to the longitudinal axis of the distal tube of the irrigation sleeve.

8. The irrigation sleeve of claim 5, wherein the irrigation sleeve comprises a plurality of ribs distributed circumferentially around the internal surface of the distal end of the distal tube of the irrigation sleeve.

9. The irrigation sleeve of claim 5, wherein the irrigation sleeve including the at least one rib is comprised of an elastomeric material.

10. An irrigation sleeve for an ophthalmic instrument, the irrigation sleeve comprising:
   a proximal hub adapted to be coupled to a housing of the ophthalmic instrument; and
   a distal tube adapted to fit around a working tip of the ophthalmic instrument, the distal tube having a longitudinal axis, a distal end, an end opening at the distal end of the distal tube adapted to fit around a distal end of the working tip projecting therethrough, and a side opening at the distal end of the distal tube proximate to the end opening;
      wherein the irrigation sleeve comprises an elastomeric material and wherein the irrigation sleeve has been subjected to one or more manufacturing steps adapted to stiffen the irrigation sleeve;
   wherein the one or more manufacturing steps include treating the irrigation sleeve by exposing the irrigation sleeve to gamma radiation; and
   wherein:
      the side opening is shaped as a teardrop comprising a point at a leading distal edge of the teardrop, two substantially straight sides extending from the leading distal edge to an area of largest width of the teardrop, and a curved trailing edge disposed opposite the leading distal edge, or
      the irrigation sleeve further comprises at least one rib on an internal surface of the distal end of the distal tube of the irrigation sleeve, the at least one rib having a length parallel to a longitudinal length of the distal tube, the length of the at least one rib corresponding with a dimension of the side opening of the distal tube.

11. The irrigation sleeve of claim 10, wherein the one or more manufacturing steps adapted to stiffen the irrigation sleeve include coating the irrigation sleeve with a stiffening coating.

12. The irrigation sleeve of claim 11, wherein the stiffening coating is a parylene coating.

13. The irrigation sleeve of claim 5, wherein a cross-section of the at least one rib is at least one of trapezoidal, rounded, or triangular shape.

14. The irrigation sleeve of claim 11, wherein the stiffening coating has a thickness of about 5 microns.

15. The irrigation sleeve of claim 1, wherein the distal tube comprises a bend at the distal end.

* * * * *